US012599561B2

(12) United States Patent
Bushman

(10) Patent No.: US 12,599,561 B2
(45) Date of Patent: Apr. 14, 2026

(54) LOCALIZED IMMUNOSUPPRESSION OF ALLOGRAFTS FOR PERIPHERAL NERVE REPAIR

(71) Applicant: UNIVERSITY OF WYOMING, Laramie, WY (US)

(72) Inventor: Jared Bushman, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 812 days.

(21) Appl. No.: 17/857,590

(22) Filed: Jul. 5, 2022

(65) Prior Publication Data

US 2022/0339104 A1 Oct. 27, 2022

Related U.S. Application Data

(62) Division of application No. 16/049,343, filed on Jul. 30, 2018, now Pat. No. 11,376,219.

(51) Int. Cl.
| | |
|---|---|
| *A61K 9/14* | (2006.01) |
| *A61K 9/06* | (2006.01) |
| *A61K 31/436* | (2006.01) |
| *A61K 31/57* | (2006.01) |
| *C07K 16/28* | (2006.01) |

(52) U.S. Cl.
CPC ................ *A61K 9/146* (2013.01); *A61K 9/06* (2013.01); *A61K 31/436* (2013.01); *A61K 31/57* (2013.01); *C07K 16/2809* (2013.01)

(58) Field of Classification Search
None
See application file for complete search history.

(56) References Cited

U.S. PATENT DOCUMENTS

| | | | | |
|---|---|---|---|---|
| 8,734,848 | B2 * | 5/2014 | Pandit | A61K 49/0054 424/489 |
| 10,064,938 | B2 * | 9/2018 | Bushman | C07K 16/18 |
| 10,588,970 | B2 * | 3/2020 | Bushman | A61L 27/48 |
| 10,682,408 | B2 * | 6/2020 | Bushman | C07K 16/2866 |
| 10,980,880 | B2 * | 4/2021 | Bushman | A61K 45/06 |
| 2003/0040112 | A1 | 2/2003 | Muir | |
| 2004/0063610 | A1 | 4/2004 | Gold | |
| 2005/0238625 | A1 | 10/2005 | Chancellor et al. | |
| 2010/0204683 | A1 | 8/2010 | Bodor et al. | |
| 2014/0112960 | A1 * | 4/2014 | Lin | A61K 47/34 424/93.1 |
| 2017/0258901 | A1 | 9/2017 | Bushman | |

FOREIGN PATENT DOCUMENTS

WO WO-2016198238 A1 * 12/2016 ............. A61K 47/10

OTHER PUBLICATIONS

Schexnailder, P., Schmidt, G. Nanocomposite polymer hydrogels. Colloid Polym Sci 287, 1-11 (2009). https://doi.org/10.1007/s00396-008-1949-0. (Year: 2008).*
Geng et al. (2011). Sustained release of VEGF from PLGA nanoparticles embedded thermo-sensitive hydrogel in full-thickness porcine bladder acellular matrix. Nanoscale research letters, 6(1), 312. https://doi.org/10.1186/1556-276X-6-312. (Year: 2011).*
Gergori. (2015). Clinical Outlook for Type-1 and FOXP3(+) T Regulatory Cell-Based Therapy. Frontiers in immunology, 6, 593. https://doi.org/10.3389/fimmu.2015.00593. (Year: 2015).*
Li. (2016). Designing hydrogels for controlled drug delivery. Nature reviews. Materials, 1(12), 16071. https://doi.org/10.1038/natrevmats.2016.71. (Year: 2016).*
Elzoghby. Natural Polymeric Nanoparticles for Brain-Targeting: Implications on Drug and Gene Delivery. Curr Pharm Des. 2016;22(22):3305-23. doi: 10.2174/1381612822666160204120829. (Year: 2016).*
Mohammad. An Overview of Chitosan Nanoparticles and Its Application in Non-Parenteral Drug Delivery. Pharmaceutics. Nov. 20, 2017;9(4):53. doi: 10.3390/pharmaceutics9040053. (Year: 2017).*
Mekaj et al., Application of topical pharmacological agents at the site of peripheral nerve injury and methods used for evaluating the success of the regenerative process. Journal of Orthopaedic Surgery and Research 2014 9:94.
Rice et al., Exogenously Triggered, Enzymatic Degradation of Photopolymerized Hydrogels With Polycaprolactone Subunits: Experimental Observation and Modeling of Mass Loss Behavior, Biomacromolecules, Jun. 2006 ; 7(6): 1968-1975. doi:10.1021/bm060086+.

(Continued)

*Primary Examiner* — Daniel E Kolker
*Assistant Examiner* — Julia A Rossi
(74) *Attorney, Agent, or Firm* — Patterson + Sheridan, LLP

(57) ABSTRACT

Embodiments described herein relate to restorative solutions for segmental peripheral nerve (PN) defects using allografted PNs for stimulating PN repair. More specifically, embodiments described herein provide for localized immunosuppression (LIS) surrounding PN allografts as an alternative to systemically suppressing a patient's entire immune system. Methods include localized release of immunosuppressive (ISV) agents are contemplated in one embodiment. Methods also include localized application of immunosuppressive (ISV) regulatory T-cells (Tregs) and/or mesenchymal stomal cells in other embodiments. Hydrogel carrier materials are also described herein.

12 Claims, 6 Drawing Sheets

(56)                    References Cited

OTHER PUBLICATIONS

Zustiak, et al, Hydrolytically degradable opoly(ethelyne glycol) hydrogel scaffolds with tunable degradation and mechanical properties, Biomacromolecules. May 10, 2010; 11(5): 1348-1357. doi:10.1021/bm100137q.

Maeda, Structures and Applications of Thermoresponsive Hydrogels and Nanocomposite-Hydrogels Based on Copolymers with Poly (Ethylene Glycol) and Poly (Lactide-Co-Glycolide) Blocks, Bioengineering. Nov. 21, 2019; 6(4), 107. https://doi.org/10.3390/bioengineering6040107.

Dhungana, S., et al.—Isolation and characterization of regulatory T cells for localized immunosuppression of allografts, presentation exhibited at the 2nd Annual Wyoming IDeA Networks for Biomedical Research Excellence Conference Apr. 27-29, 2017, Laramie, Wyoming, 1 page.

Li, Dongmei—Utilizing Oxygen-Inhibited Photopolymerization to Control Size of Multimodal PEGDA Hydrogel Particles, presentation exhibited at the 2nd Annual Wyoming IDeA Networks for Biomedical Research Excellence Conference, Apr. 27-29, 2017, Laramie, Wyoming, 41 pages, with Abstract, 2 pages.

Wyoming INBRE 2nd annual wyoming idea networks for biomedical research excellence conference, Apr. 27-29 in Laramie WY ( Year: 2017).

Somashekar, Chitosanases—Properties and Applications:A Review, Bioresource Technology 55 ( 1996) 35-45 (Year: 1996).

Wikipedia "lipid metabolism" accessed Jul. 18, 2020 from wikipedia.org (Year: 2020).

Karkar, Designing degradable hydrogels for orthogonal control of cell microenvironments, Chem. Soc. Rev., 2013, 42, 7335 (Year: 2013).

Rapport "the hydrolysis of hyaluronic acid by pneumococcal hyaluronidase" (Year: 1951).

Li and Mooney, Designing hydrogels for controlled drug delivery Nat Rev Mater. Dec. 2016 ; 1 ( 12) (Year: 2016).

* cited by examiner

LOCALIZED IMMUNOSUPPRESSION OF ALLOGRAFTS FOR PERIPHERAL NERVE REPAIR

CROSS-REFERENCE TO RELATED APPLICATIONS

This application is a divisional of and claims benefit to U.S. patent application Ser. No. 16/049,343, filed Jul. 30, 2018, now U.S. Pat. No. 11,376,219, which is hereby incorporated by reference in its entirety.

GOVERNMENT RIGHTS

This invention was made with government support under GM103432 awarded by the National Institutes of Health. The government has certain rights in the invention.

BACKGROUND

Field

Embodiments of the present disclosure generally relate to methods and materials for peripheral nerve (PN) repair.

Description of the Related Art

Peripheral nerves (PNs) branch extensively through the body and are fundamental for motor control, sensation, and function of organ systems. Conventional treatment for segmental PN defects include direct coaptation of nerve stumps, insertion of a mixed (motor+sensory) PN autograft, autografted sensory nerves, decellularized/processed allografted nerves, and biodegradable conduits.

Conduits and processed (decellularized) allografts are not currently capable of matching the regeneration associated with sensory autografts (typically the sural nerve), which is typically considered the clinical standard for PN regeneration. PN autografts require a secondary surgery with significant associated morbidity. Moreover, PN autografts suffer from a limited supply of correctly sized nerves. Size mismatch leads to formation of neuromas and poor functional regeneration.

Mixed PN autografts stimulate superior nerve regeneration when compared to sensory autografts, however, mixed nerves are not viable autograft options in most clinical cases. Schwann cells that myelinate motor or sensory axons intrinsically differ with one another, as Schwann cells that associate with motor axons differentially express several biomolecules that facilitate axon growth and guiding motor axons to correctly reinnervate motor branch points. As a result, sensory grafts that lack motor-associated Schwann cells are not an optimal solution for repair of mixed PNs. An additional limitation of autografts and bioengineered strategies is that neither option is ideally suited to bridge segmental nerve defects of complex nerve structures, such as defects that encompass branch points.

PN allografts are contemplated as a solution to the limitations of PN autografts. While harvesting and screening of donor tissue has advanced considerably, continual systemic immunosuppression (SIS) carries substantial risks of opportunistic infections, renal damage, and post-transplant lymphoproliferative disorders. Patient compliance can also be problematic as many patients fail to adhere to their immunosuppressive treatment regimens, resulting in graft failure. These risks outweigh the potential benefit of allografted PNs.

Hundreds of thousands of injuries to PNs occur each year that require surgical intervention. Thus, what is needed in the art are improved methods and materials for peripheral nerve repair.

SUMMARY

In one embodiment, a pharmaceutically acceptable carrier material is provided. The material includes a hydrogel material comprising one or more of extracellular matrix, collagen, alginate, agarose, peptide-based hydrogels, hyaluronic acid, hyaluronan, keratin, fibronectin, dermatan, poly(sialic acid), fibrin, chitosan, chitin, cholic acid, dextran, dextrin, cellulose, gelatin, gelatinous protein mixtures, laminin, perlecan, aggrecan, glycosaminoglycans, heparin, cholesterol, chondroitin sulfate, polycholesterol, hydroxyapatite, silk, bisphosphonates, tricalcium phosphate, sacran, decellularized extracellular matrix, xanthan gum, starch, pectin, amylopectin, amylose, elastin, chemically modified derivatives thereof, and combinations and mixtures thereof. The material also includes polymeric nanoparticles disposed in the hydrogel material and one or more of immunosuppressive agents, Tregs, antibodies, mesenchymal stomal cells, and cells disposed in the polymeric nanoparticles.

In another embodiment, a pharmaceutically acceptable carrier material is provided. The material includes a hydrogel material hydrogel comprising one or more of poly (glutamic acid), poly(propylene fumarate), poly(N-hydroxyethyl)-DL-aspartamide, propylene glycol, poly(ethylene oxide), poly(propylene oxide), poly(vinyl alcohol), poly (acrylic acid), poly(hedral oligosilsesquioxane), poly(methacrylic acid), poly(vinyl-pyrrolidone), polyacrylamide, poly (isopropylacrylamide), polyphosphazene, peptides, polyaldehyde, tyrosine-derived polycarbonates, methacrylate, polymethacrylate, N-isopropylacrylamide, acrylamide, acrylate, polyacrylate, poly(lactic acid), poly(glycolic acid), poly(lactide-co-glycolide), poly(3,4-ethylenedioxythiophene), graphene oxide, poly(graphene oxide), polycaprolactone, sodium dodecyl sulfate, vinyl phosphonic acid, poly-dimethylsiloxane, titanium, bioactive glass, carbon nanotubes, silicone, silica, thiolene materials, chemically modified derivatives thereof, and combinations and mixtures thereof. The material also includes polymeric nanoparticles disposed in the hydrogel material and one or more of immunosuppressive agents, Tregs, antibodies, mesenchymal stomal cells, and cells disposed in the polymeric nanoparticles.

In yet another embodiment, a pharmaceutically acceptable carrier material is provided. The material includes a hydrogel material comprising three distinct materials arranged as triblock copolymers selected from the group consisting of poly(glutamic acid), poly(propylene fumarate), poly(N-hydroxyethyl)-DL-aspartamide, propylene glycol, poly(ethylene oxide), poly(propylene oxide), poly(vinyl alcohol), poly(acrylic acid), poly(hedral oligosilsesquioxane), poly(methacrylic acid), poly(vinyl-pyrrolidone), polyacrylamide, poly(isopropylacrylamide), polyphosphazene, peptides, polyaldehyde, tyrosine-derived polycarbonates, methacrylate, polymethacrylate, N-isopropylacrylamide, acrylamide, acrylate, polyacrylate, poly(lactic acid), poly(glycolic acid), poly(lactide-co-glycolide), poly(3,4-ethylenedioxythiophene), graphene oxide, poly(graphene oxide), polycaprolactone, sodium dodecyl sulfate, vinyl phosphonic acid, poly-dimethylsiloxane, titanium, bioactive glass, carbon nanotubes, silicone, silica, thiolene materials, chemically modified derivatives thereof, and combinations and mixtures thereof. The material also includes polymeric nanoparticles disposed in the hydrogel material and one or more of immunosuppressive agents, Tregs, antibodies, mesenchymal stomal cells, and cells disposed in hydrogel material.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figures 1A, 1B:
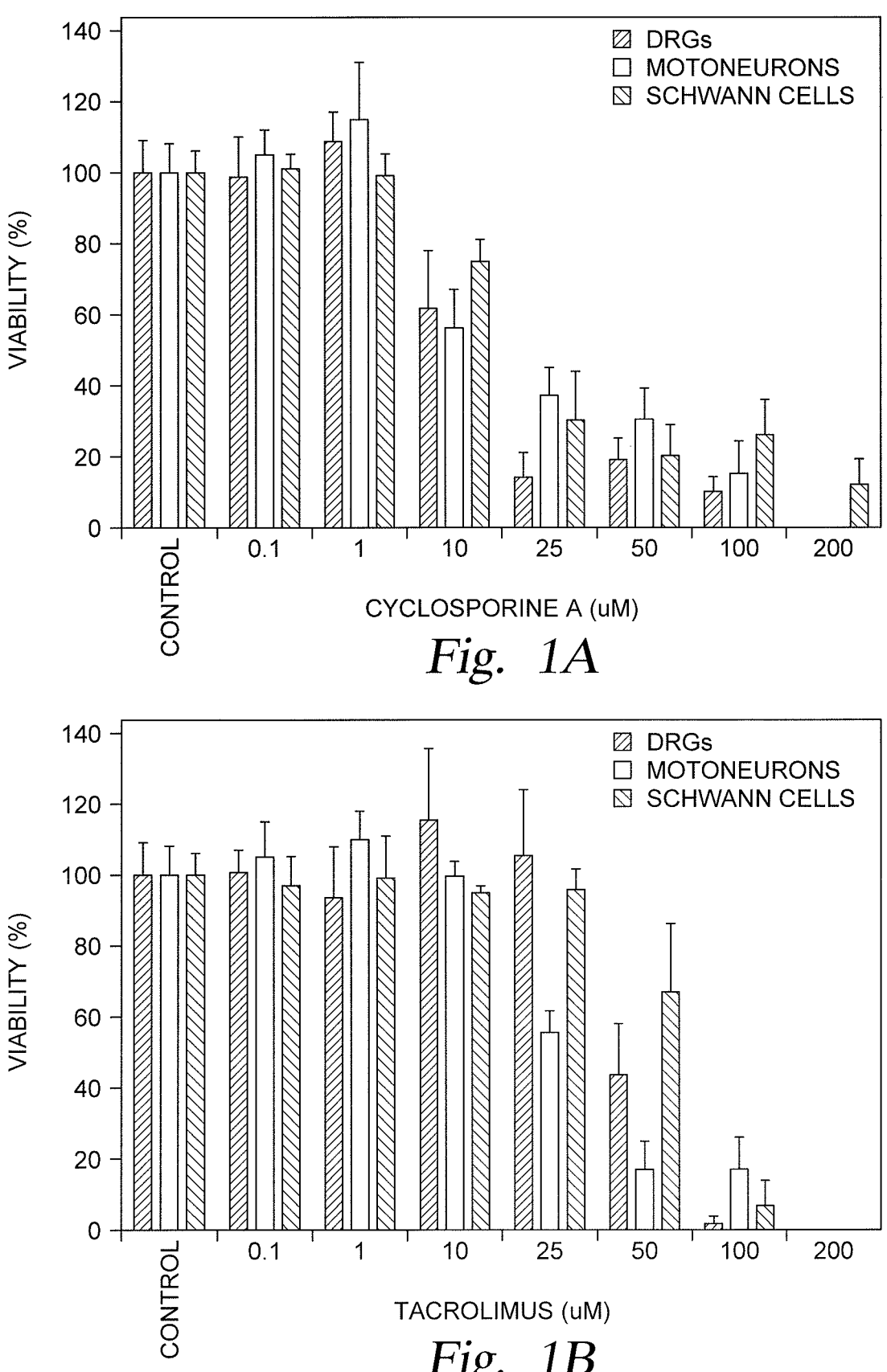
FIG. 1A illustrates data regarding the toxicity of cyclosporine A (CsA) to primary dorsal root ganglion sensory neurons (DRGs), motor neurons, and Schwann cells according to embodiments described herein.
FIG. 1B illustrates data regarding the toxicity of tacrolimus to DRGs, motor neurons, and Schwann cells according to embodiments described herein.

Embodiments described herein relate to restorative solutions for segmental peripheral nerve (PN) defects using allografted PNs for stimulating PN repair. More specifically, embodiments described herein provide for localized immunosuppression (LIS) surrounding PN allografts as an alternative to systemically suppressing a patient's entire immune system. Methods include localized release of immunosuppressive (ISV) agents are contemplated in one embodiment. Methods also include localized application of immunosuppressive (ISV) regulatory T-cells (Tregs) in other embodiments. Hydrogel carrier materials for delivery of ISV agents and are also described herein.

Localized immunosuppression is defined herein as delivering immunosuppressive agents in the local environment of a peripheral nerve allograft, thereby eliminating or minimizing the utilization of immunosuppressive agents for systemic delivery following implantation of a peripheral nerve allograft to treat a segmental peripheral nerve defect. Immunosuppressive agents are defined herein as therapeutics with biological activity that suppresses the activation and activity of the immune response against allografted peripheral nerve tissue. Immunosuppressive agents include, but are not limited to, small molecule therapeutics, peptides, proteins, glycans, antibodies and cells.

Methods for delivery of said immunosuppressive agents, encompassing all methods for localized delivery of said immunosuppressive agents to the allograft site, include, but are not limited to, microfluidics and catheterization to deliver agents from internal or external devices to the allograft site, implantation of biocompatible biomaterial carriers in local proximity to the allogrograft, such as, biomaterials consisting of poly(ethylene glycol), poly(lactic acid), poly(lactic-co-glycolic) acid, collagen, and fibrin, among others, that release said agents to the allograft, and other pharmaceutical formulations for localized release.

Allografts are contemplated as a solution to the limitations of PN autografts. Within an allografted PN there are the same support cells and structure as are found in autografted PNs, but allografted nerves can be mixed. Allografted mixed PNs stimulate regeneration of injured PNs to the same extent or superior to mixed autologous nerves. Allografts additionally have the potential to bridge complex segmental nerve defects, such as branch points, as PN allografts may be harvested from a donor to the exact region corresponding to the segmental defect in the recipient. Such nerves can be correctly sized for length and diameter to avoid neuromas.

Allografted PNs are distinct relative to other tissues with respect to immunosuppression (ISN). The degree of recovery promoted by allografted PNs is believed to be equally effective when systemic immunosuppression (SIS) is stopped after the axons have regenerated when compared to continuous SIS.

Schwann cells are both the major antigenic components of allografted PNs and the cell type providing much of the regenerative stimulus. It is contemplated that once the motor and sensory axons cross through the allografted nerve segment to innervate distal targets, the allogeneic Schwann cells either lower their immunogenic profile upon myelination of host axons or that the allogeneic Schwann cells can be targeted by the immune system without long lasting effects on the regenerated nerve.

It is contemplated that by delaying the immune response to the graft, a sufficient delay in the immune response to a PN allograft can be achieved through local application of immunosuppressants instead of systemic application of immunosuppressants. Localized immunosuppression minimizes the risks associated with ISV therapy. For example, local administration of ISV agents leaves the immune response in the rest of the body largely intact. In addition, lower doses of ISV agents administered locally are much less likely to cause kidney damage as comparatively negligible amounts of ISV agents enter the circulatory system.

Still further, localized and temporary immunosuppression is much less likely to contribute to causing lymphoproliferative disorders. Moreover, patient compliance is not a concern if sufficient administration of immunosuppressive agents for the entire recovery period can be applied during initial surgery. It is believed that allografted PNs may improve functional recovery of segmental PN defects because allografted PNs take advantage of temporary immunosuppression, thereby facilitating clinical adoption for PN repair.

It is also contemplated that localized immunosuppression through localized delivery of immunosuppressive agents will remove or minimize utilization of systemic immunosuppression. For example, instead of daily systemic immunosuppression for peripheral nerve allografts during the initial regeneration period, systemic immunosuppression may be delivered on a less frequent basis, thus, improving the quality of care for the patient and improving prospects for patient compliance.

Acute rejection of nerve transplants is primarily mediated by T-cells. Following transplantation of a nerve segment, antigen presenting cells (APCs) of donor or host origin activate host T-cells by displaying alloantigens via major-histocompatibility complex (MHC) molecules to the $\alpha\beta$T-cell receptors (TCRs) of T-cells, with CD4+ and CD8+ T-cells the primary effector T-cells. Activation of T-cells by APCs can occur locally to the site of the allograft, however, activation of T-cells is more robust when the APCs migrate to a lymphatic center. Chronic rejection occurring over months to years involves B-cell activation and progressive infiltration of macrophages into the graft vasculature. As PN allografts utilize the benefits of temporary immunosuppression, which may span weeks to months, it is contemplated that PN allografts are not subject to functional impairment associated with the timeline of chronic rejection. Accordingly, embodiments described herein provide for a reduced response of effector T-cells to enable PN allograft acceptance via localized immunosuppression.

Calcineurin inhibitors (CNIs), such as cyclosporine A (CsA) and tacrolimus (examples of immunosuppressive agents), are contemplated for utilization with PN allograft transplantation. CNIs prevent activation of T-cells by binding to immunophilins and increasing their affinity for calcineurin, thereby inhibiting calcineurin activation of NFAT and NFkB transcription. CNIs are also associated with preventing or reducing production of IL-2 and other immune activating cytokines. Interestingly, both tacrolimus and CsA have neuroprotective effects even in the absence of transplanted cells or tissues.

Prednisolone is the active form of the glucocorticoid prednisone, a pro-drug metabolized into prednisolone, which may be utilized as another example of an immunosuppressive agent and may be utilized for PN allografts according to embodiments described herein. Prednisolone may also be utilized in combination with CNIs for PN allografts in other embodiments. Anti T-cell antibodies, mammalian or otherwise, are also contemplated for localized immunosuppression to protect against the eventuality that APCs will migrate to lymphatic centers and activate effector T-cells outside of the zone of localized immunosuppression. Suitable anti T-cell antibodies for utilization in human subjects include, but are not limited to ATGAM, visilizumab, alemtuzumab, basiliximab, and daclizumab, among others.

Binding of anti T-cell antibodies (such as R73 and MRC Ox-8, rat model described infra) to $\alpha\beta$TCRs on CD4+ and CD8+ cells mitigates the risk of APC migration. Moreover, anti T-cell antibodies may substantially prevent or reduce TCR-MHC binding and target T-cells for depletion via opsonization for phagocytosis or lysis due to complement activation against the T-cell. Tacrolimus, prednisolone, and anti T-cell antibodies referred to herein are also contemplated within the definition of immunosuppressive agents.

Tregs are a sub-population of CD4+ cells and suppress activated effector T-cells through a variety of mechanisms linked to Treg FoxP3 expression. Generally, Tregs function of APCs and effector T-cell populations and proliferate in response to IL-2 and down-regulate the adaptive immune response of effector T-cells. Tregs also attenuate graft versus host disease and a number of other autoimmune disorders. Accordingly, embodiments described herein contemplate local application of Tregs for suppression of an acquired immune response to PN allografted tissue. In addition, mesenchymal stomal cells (MSCs) are also an immunosuppressive cell type contemplated for localized delivery suppress the immune response to allografted PNs as MSCs attenuate many autoimmune diseases and deactivate effector T-cells.

Figure 1C:
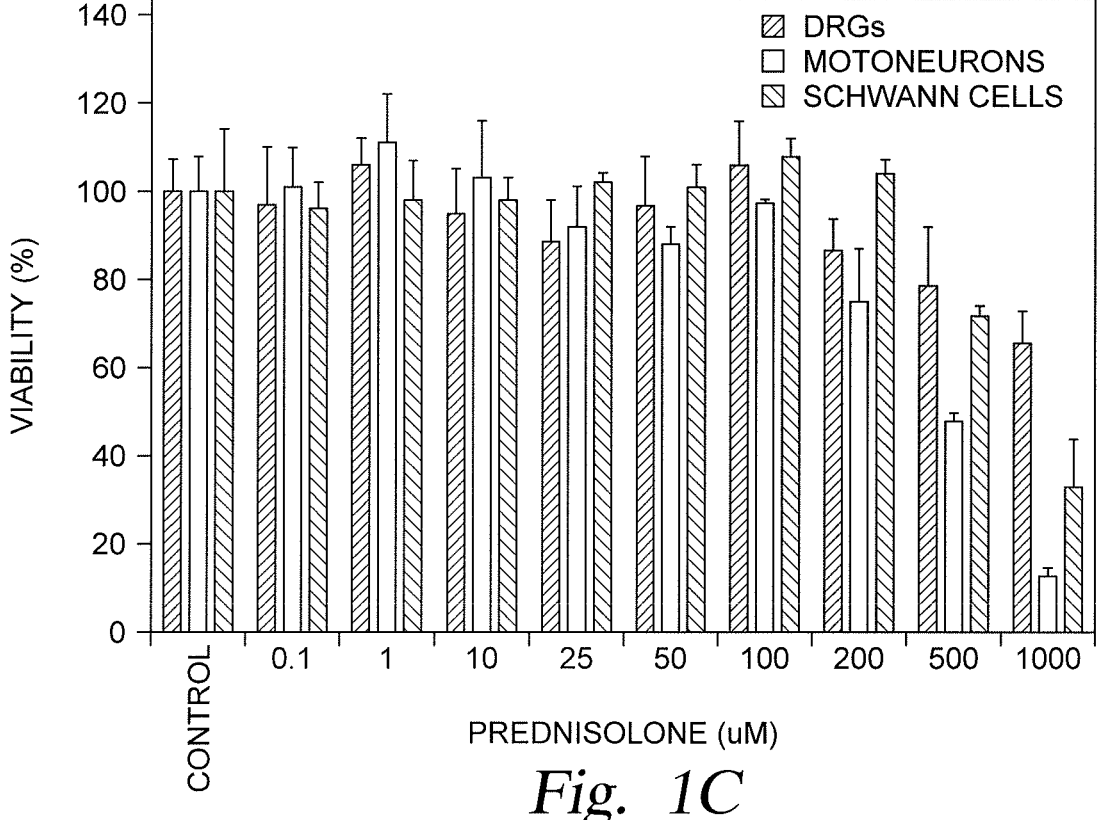
FIG. 1C illustrates data regarding the toxicity of prednisolone to DRGs, motor neurons, and Schwann cells according to embodiments described herein.

It is contemplated that delivery of immunosuppressive agents function within a favorable therapeutic window. PNs are comprised of three major nervous system cell types, motor neurons, sensory neurons, and Schwann cells. FIG. 1A illustrates data regarding the toxicity of CsA to dorsal root ganglion sensory neurons (DRGs), motor neurons, and Schwann cells. FIG. 1B illustrates data regarding the toxicity of tacrolimus to DRGs, motor neurons, and Schwann cells. FIG. 1C illustrates data regarding the toxicity of prednisolone to DRGs, motor neurons, and Schwann cells.

Cells (DRGs, motor neurons, and Schwann cells) were cultured for 72 hours in various concentration of the immunosuppressive drugs and viability was evaluated using the Alamar blue viability assay. ISV's were diluted into media using a maximum of 1% dimethylsulfoxide (DMSO). The results indicated in FIG. 1A indicate that CsA is tolerated by the cells at doses up to about 1 μM, which is significantly greater than the effective dose of CsA (about 25 μM) for inhibiting activation and proliferation of the immune cells.

Figures 2A, 2B:
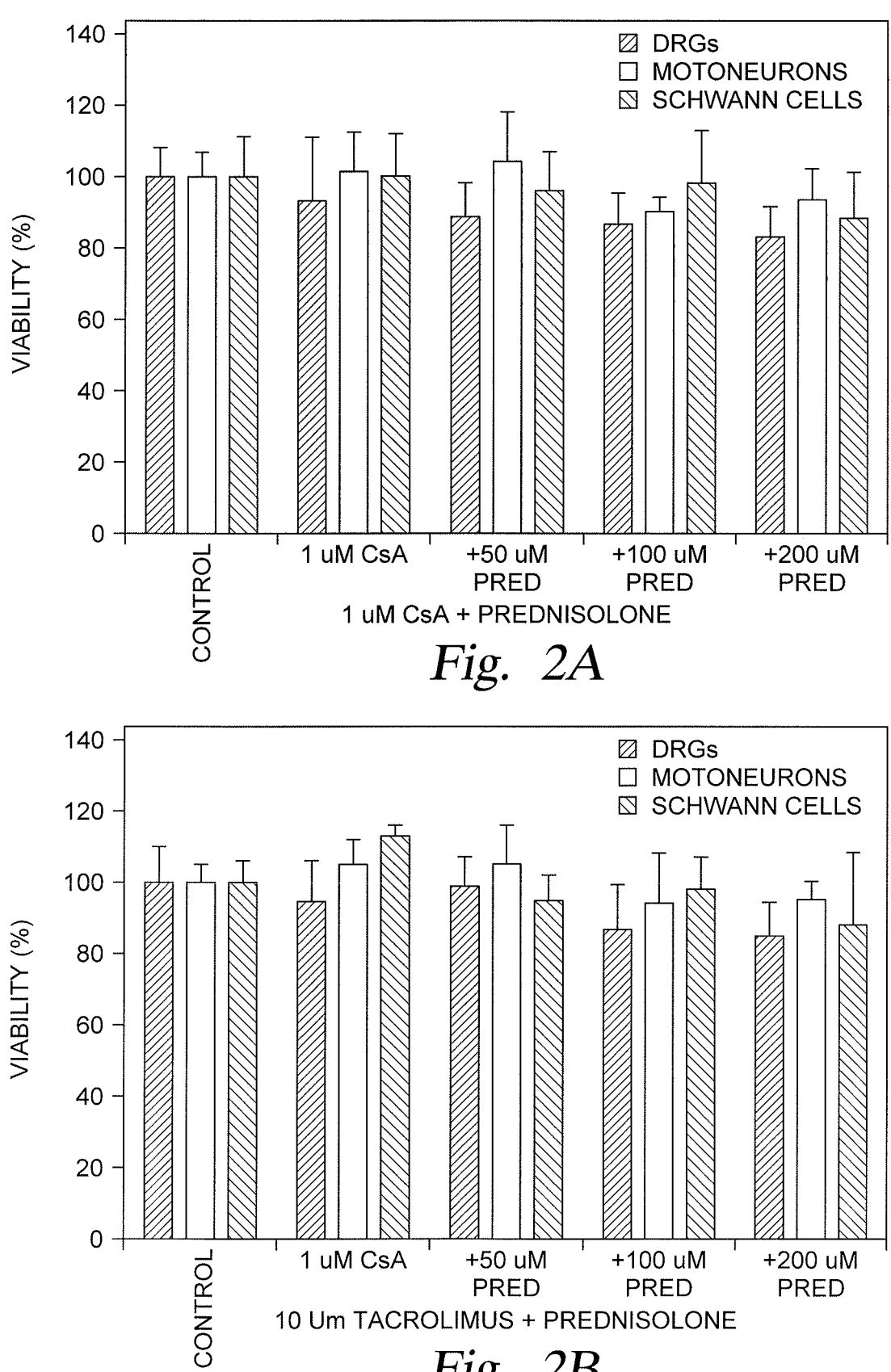
FIG. 2A illustrates data regarding the viability of DRGs, motor neurons, and Schwann cells cultured in about 1 µM CsA with differing concentrations of prednisolone according to embodiments described herein.
FIG. 2B illustrates data regarding the viability of DRGs, motor neurons, and Schwann cells cultured in about 10 µM tracrolimus with differing concentrations of prednisolone according to embodiments described herein.

The results indicated in FIG. 1B indicate that tacrolimus is tolerated by the cells at doses up to between about 10 μM and about 25 μM, which is greater than the effective dose of tacrolimus (between about 50-100 μM) for inhibiting activation and proliferation of immune cells. The results indicated in FIG. 1C indicate that prednisolone is tolerated by the cells at doses up to about 200 μM, which is greater than the effective dose of prednisolone (greater than about 240 μM) for inhibiting activation and proliferation of immune cells FIG. 2A illustrates data regarding the viability of DRGs, motor neurons, and Schwann cells cultured in about 1 μM CsA with differing concentrations of prednisolone. FIG. 2B illustrates data regarding the viability of DRGs, motor neurons, and Schwann cells cultured in about 10 μM tacrolimus with differing concentrations of prednisolone. In other words, the cells were exposed to the highest tolerated doses of CsA and tacrolimus with increasing doses of prednisolone and no toxicity was observed. Thus, it is contemplated that CNIs may be utilized in combinations with prednisolone for localized immunosuppression.

Experimental Methods

Biological material from Sprague Dawley (GFP− and GFP+) and Lewis rats, without any pathological conditions, were utilized to determine the PN allograft methods and materials described herein. Lewis rats were obtained from Charles River Laboratories (Wilmington, MA) and Sprague Dawley rats were obtained from Rat Resource and Research Center (Columbia, MO). Alzet osmotic pumps (model 1004), commercially available from DURECT Corporation, Cupertino, CA, were utilized for delivery of immunosuppressive agents to PN allografts.

For animal experiments, Sprague Dawley (SD) PN allografts were implanted within Lewis recipients, which are respectively RT1[1] and RT1[b] for major histocompatibility complex (MHC). Donor sciatic nerves are harvested from SD rats under isofluorane anesthesia and connective and other non-nerve tissue was removed. Under sterile "no touch" techniques, the left sciatic nerve of recipient Lewis rats was exposed and a segment of the host nerve was removed that corresponds to a length of the allograft being inserted, spanning approximately 2 mm distal for the length of the allografted segment to be inserted. 9-0 sutures are used to insert the SD allograft PN.

After suturing the allograft PN into place, osmotic pumps were implanted subcutaneously approximately 2 cm lateral to the surgical cavity. A polyethylene catheter extends from the pump into the tissue cavity, where it is sutured to the suture line that closes the musculature, with approximately 0.75 cm of the catheter remaining within the cavity to release ISV agents. The osmotic pump released 0.11 μl/hr of solution for 28-38 days. The positive control group of daily systemic immunosuppression received intraperotineal (IP) injections of 1 mg/kg tacrolimus the day before surgery and every day thereafter. LIS and vehicle control (70% DMSO 30% PBS) received IP injections of tacrolimus the day before and the day of surgery.

To extrapolate the in vitro effective and tolerated doses of ISV agents to PN and immune cells to a dynamic in vivo environment, the tissue cavity with the sciatic nerve contained 190±22 μl of fluid after suturing the muscles together. This figure was used for the volume in dosage calculations. Several assumptions were made regarding the flow of interstitial fluid (i.e. turnover within the cavity) in order to calculate drug loading. Based on the osmotic pressure in rat skeletal muscles (−1 to −3 mm Hg) compared to −0.20 mm Hg for the overall body average, brain tissues ranging from +3 to +8 mm Hg and the rate of lymphatic turnover in general, it was postulated that the fluid within the cavity containing the allograft and pump would turnover hourly. On the basis of these measurements, the experiment with parameters outlined in Table 1 was performed.

TABLE 1

| ISV agent | in vitro effective concentration on immune cells | Measures in vitro tolerated concentrations on PN cells | Effective clinical plasma concentration | Targeted concentration within the nerve cavity | Concentrations loaded with implanted osmotic pump |
|---|---|---|---|---|---|
| Tacrolimus | 0.5-1.0 nM | 10-25 μM | 21 nM | 5 μM | 9 mM |
| Prednisolone | 240 nM | 200 μM | 277 nM | 50 μM | 90 mM |
| Anti-TCR antibody | 10 ng/ml | N/A | N/A | 165 ng/ml | 30 μg/ml |

Rats were sacrificed after 1, 4, 6, and 16 weeks following surgery. Longitudinal sections of the nerves were cut and labeled for markers of axons ($\beta$-III tubulin—Abcam 1:200) and T-cells (R73—Cederlane Laboratories 1:200). Sections showed that regeneration of axons into the allografts in recipients of LIS was comparable to the positive control of daily SIS. After 1 week, host axons had crossed into the allografts of SIS and LIS recipient animals in line with the organization of the nerve. In contrast, $\beta$-III tubulin stains in no ISN and vehicle control animals showed a disorganization of axons and denser accumulation of fibrous tissue at the donor-host boundary as illustrated in FIGS. 3A and 3C.

Figure 3A:
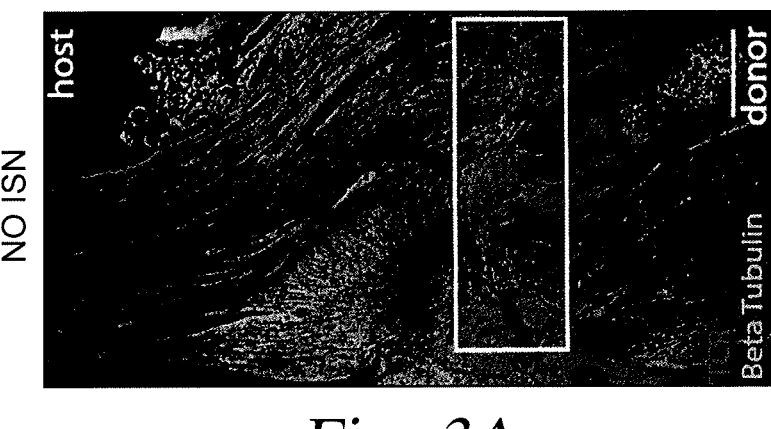
FIG. 3A illustrates a micrograph of a β-III tubulin stained allograft with no immunosuppression according to embodiments described herein.
Figure 3B:
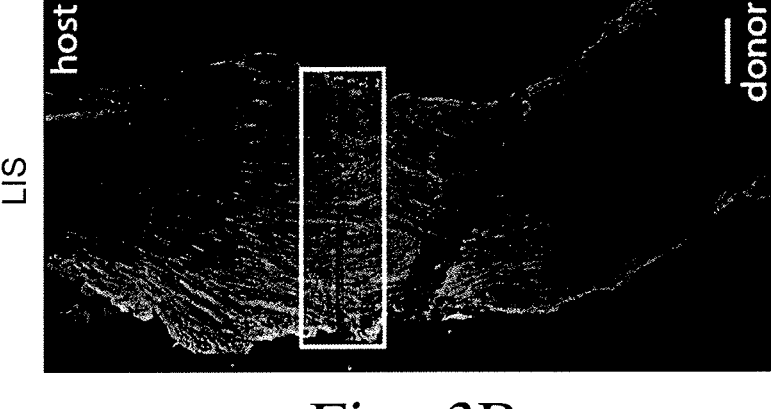
FIG. 3B illustrates a micrograph of a β-III tubulin stained allograft with localized immunosuppression according to embodiments described herein.

After 28 days, allografts with LIS showed axons extending in line from the host nerve into and through the allograft as illustrated in FIG. 3B. The proximal and distal host-donor boundaries, as determined by identifying the proximal and distal suture points, were histologically indistinguishable in LIS recipients, indicating a functional merger of tissues.

Figure 3C:
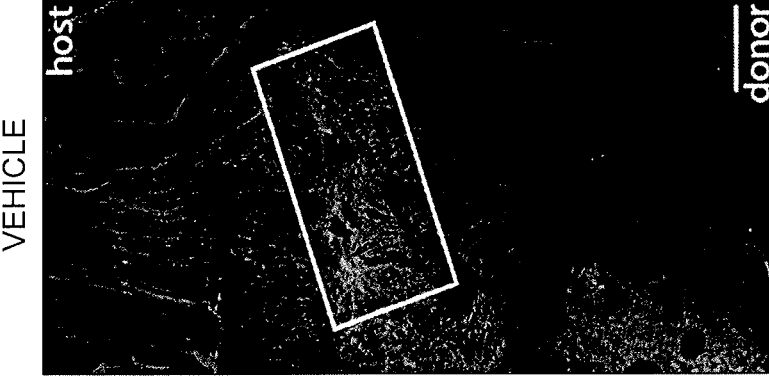
FIG. 3C illustrates a micrograph of a β-III tubulin stained allograft vehicle according to embodiments described herein.

In contrast, negative control groups of vehicle and no ISN showed a lack of axonal crossing into the allograft and robust accumulation of T-cells and apparent scar tissue at the donor-host boundary as illustrated in FIGS. 3A and 3C. Fluorescent densitometry of $\beta$-III tubulin was conducted for 10 randomly selected sections within 1 cm$^2$ segments, taking the ratio of the signal within the allograft to the proximal host structure, showing a 78±11% reduction in signal intensity of $\beta$-III tubulin in the allograft regions of vehicle controls compared to LIS. Accordingly, it is believed that LIS for 28 days is effective at promoting robust regeneration of host axons into allografted PNs, while the negative controls exhibit graft rejection and lack of host axonal entry into the graft which is indicative of long-term graft failure.

Figure 4A:
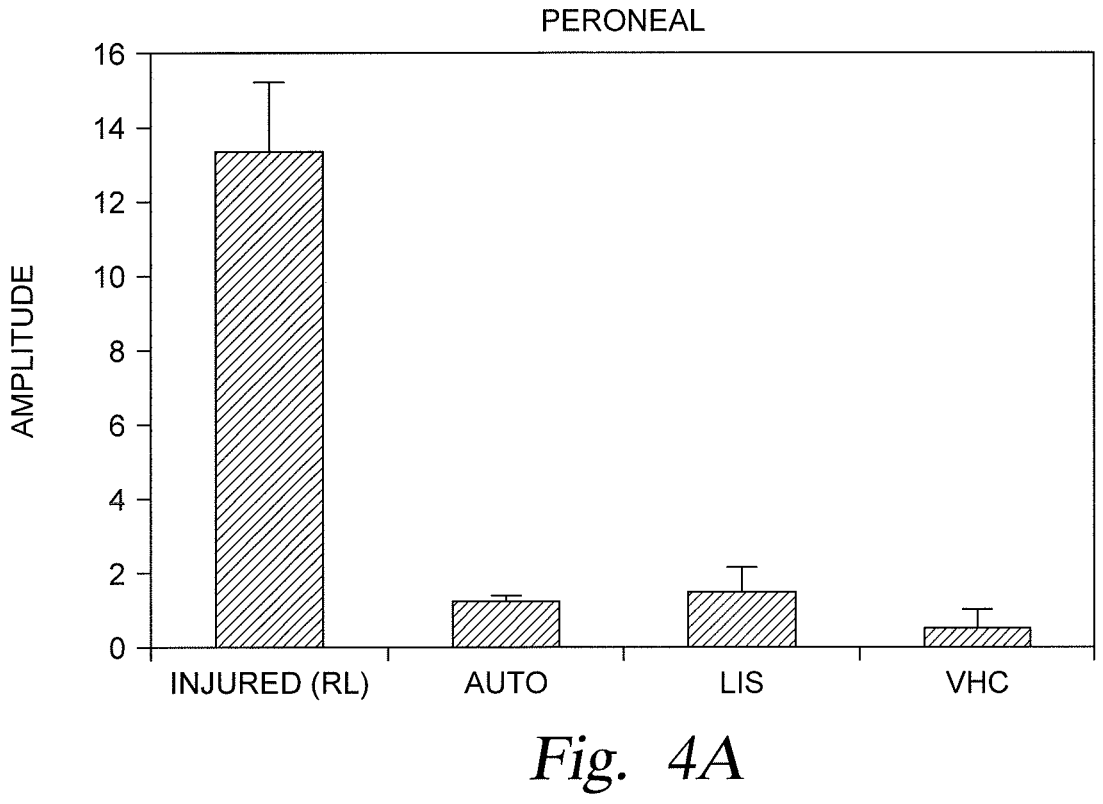
FIG. 4A illustrates compound muscle action potential data of the peroneal branch of the sciatic nerve after PN allograft repair according to embodiments described herein.
Figure 4B:
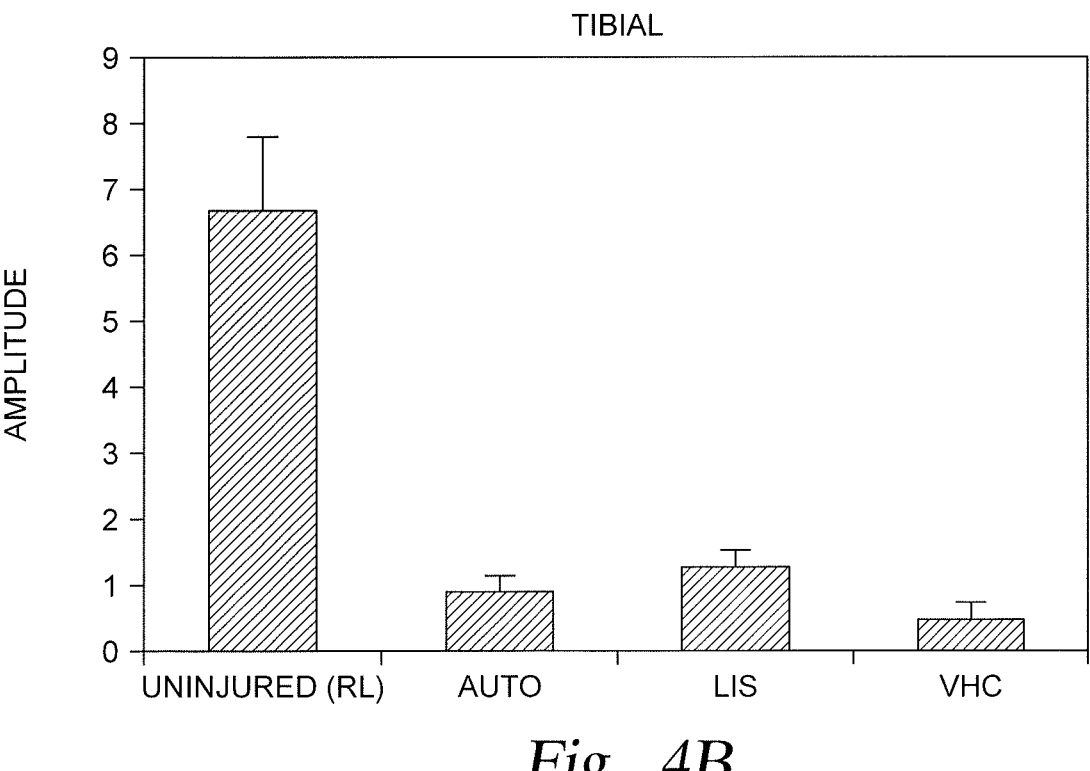
FIG. 4B illustrates compound muscle action potential data of the tibial branch of the sciatic nerve after PN allograft repair according to embodiments described herein.

FIG. 4A illustrates compound muscle action potential (CMAP) data of the peroneal branch of the sciatic nerve after PN allograft repair in the rat experiment described above. FIG. 4B illustrates compound muscle action potential data of the tibial branch of the sciatic nerve after PN allograft repair. CMAPs (electrophysiological measurements) were obtained at the dorsal and planta foot muscles, which are the most distal reinnervation targets of the peroneal and tibial branches of the sciatic nerve. CMAP amplitude measures the strength of nerve signal conduction and corresponds to the number of conducting axons of the regenerated nerve that reached the muscles.

FIG. 4A data, which is based on CMAP tests of the peroneal branch of the sciatic nerve 16 weeks post PN allograft, indicates that PN allografts utilizing localized immunosuppression were at least equivalent to autologous grafts and better than the vehicle. FIG. 4B data, which is based on CMAP tests of the tibial branch of the sciatic nerve 16 weeks post PN allograft, indicates that PN allografts utilizing localized immunosuppression were at least equivalent to autologous grafts and better than the vehicle. Accordingly, it can be seen that localized immunosuppression utilized with a PN allograft provides for desirable PN regeneration without the risks of systemic immunosuppression.

Materials for ISV Agent Delivery

Embodiments described herein provide for materials for ISV agent delivery in a biological system. Materials described herein are contemplated to enable ISV agent delivery for an amount of time greater than one month, such as 2 months or greater. Further, the materials described herein provide an encapsulant that delivers Tregs and/or MSCs to the PN allograft. The materials are contemplated to enable controlled release profiles of ISV agents, Tregs, antibodies, MSCs, and cells, via characteristics of the material composition. A degradation motif, a macromolecular structure, a macromere mass fraction, and a particle size distribution are controllable to enable continual and controlled release of the ISV agents, Tregs, antibodies, MSCs, and cells. Moreover, the materials described herein exhibit desirable mechanical flexibility and strain moduli for in vivo application, biodegradability, and bioresorbability, thus, providing additional benefits for a wide range of nerve repair application with reduced morbidity risks.

Microfluidic co-emulsification of biomaterials, ISV, Tregs, antibodies, MSCs, and cells enables fabrication of layered particles and confers versatility for application in PN allograft systems with localized immunosuppression. In one embodiment, hydrophobic small molecule therapeutics are formulated into surface-eroding, poly(lactic-co-glycolic acid) (PLGA) polymeric nanoparticles, which are subsequently doped into bulk-eroding material fabricated from poly(ethylene glycol) (PEG) diacrylate (PEG-DA) or poly (ethylene glycol) norbornene (PEG-NB). Thus, nanoparticles are dispersed into a bulk hydrogen material. In one embodiment, the surface-eroding nanoparticles are fabricated from a hydrogel material. In another embodiment, the bulk-eroding material is fabricated from a hydrogel material. In one embodiment, the surface-eroding nanoparticles and the bulk-eroding material are fabricated from the same hydrogel material. Alternatively, the surface-eroding nanoparticles and the bulk-eroding material are different hydrogel materials.

In one embodiment, the hydrogel utilized for the bulk-eroding material is a photopolymerizable hydrogel, however, it is contemplated that other polymerization techniques may be utilized in accordance with the embodiments described herein. For example, the hydrogel material may be a thermally polymerizable hydrogel and/or a chemically polymerizable hydrogel. In another embodiment, the hydrogel utilized for the polymeric nanoparticles is a photopolymerizable hydrogel. The disclosure of Methods of Generating Microparticles and Porous Hydrogels Using Microfluidics in U.S. patent application Ser. No. 15/335,184 is hereby incorporated by reference in its entirety.

Hydrogel materials, which are pharmaceutically acceptable carriers for the various ISV agents, Tregs, antibodies, MSCs, and cells described above, are those materials which are considered to be substantially compatible (i.e., non-toxic or a biologically acceptable degree of toxicity) with biological tissue. In one embodiment, the hydrogel materials are hydrophilic. In another embodiment, the hydrogel materials include three-dimensional polymeric networks having polymer chains cross-linked by either covalent bonds or physical interactions, such as entanglements and/or crystallites. In one embodiment, the hydrogel materials exhibit characteristics (i.e., hydrophilicity) that enable the hydrogel materials to absorb large amounts of water or biological fluids, thus enhancing biocompatibility. In another embodiment, the hydrogel materials are degradable such that the structural components of the hydrogel materials break down over time and are capable of being absorbed by the biological system into which the hydrogel materials are incorporated. Alternatively, the hydrogel materials are non-degradable.

Natural Hydrogels

In one embodiment, the hydrogel materials are natural hydrogels which are derived from naturally occurring biomolecules synthesized by living systems. Examples of natural hydrogel materials include, but are not limited to: extracellular matrix (ECM) and chemically modified derivatives thereof; collagen and chemically modified derivatives thereof; alginate and chemically modified derivatives thereof; agarose and chemically modified derivatives thereof; peptide-based hydrogels and chemically modified derivatives thereof; hyaluronic acid and chemically modified derivatives thereof; hyaluronan and chemically modified derivatives thereof; keratin and chemically modified derivatives thereof; fibronectin and chemically modified derivatives thereof; dermatan and chemically modified derivatives thereof; poly(sialic acid) and chemically modified derivatives thereof; fibrin and chemically modified derivatives thereof; chitosan and chemically modified derivatives thereof; chitin and chemically modified derivatives thereof; cholic acid and chemically modified derivatives thereof; dextran and chemically modified derivatives thereof; dextrin and chemically modified derivatives thereof; cellulose and chemically modified derivatives thereof; gelatin and chemically modified derivatives thereof; gelatinous protein mixtures and chemically modified derivatives thereof, for example, MATRIGEL® available from Corning Life Sciences; laminin and chemically modified derivatives thereof; perlecan and chemically modified derivatives thereof; aggrecan and chemically modified derivatives thereof; glycosaminoglycans and chemically modified derivatives thereof; heparin and chemically modified derivatives thereof; cholesterol and chemically modified derivatives thereof; chondroitin sulfate and chemically modified derivatives thereof; polycholesterol and chemically modified derivatives thereof; hydroxyapatite and chemically modified derivatives thereof; silk and chemically modified derivatives thereof; bisphosphonates and chemically modified derivatives thereof, tricalcium phosphate and chemically modified derivatives thereof; sacran and chemically modified derivatives thereof; decellularized extracellular matrix and chemically modified derivatives thereof; xanthan gum and chemically modified derivatives thereof; starch and chemically modified derivatives thereof; pectin and chemically modified derivatives thereof; amylopectin and chemically modified derivatives thereof; amylose and chemically modified derivatives thereof; and elastin and chemically modified derivatives thereof.

Synthetic Hydrogels

In one embodiment, the hydrogel materials are synthetic hydrogels which are not typically synthesized by living systems in nature. Examples of synthetic hydrogel materials include, but are not limited to: poly(ethylene glycol) and chemically modified derivatives thereof; poly(glutamic acid) and chemically modified derivatives thereof; poly(propylene fumarate) and chemically modified derivatives thereof; poly(N-hydroxyethyl)-DL-aspartamide and chemically modified derivatives thereof; propylene glycol and chemically modified derivatives thereof; poly(ethylene oxide) and chemically modified derivatives thereof; poly(propylene oxide) and chemically modified derivatives thereof; poly(vinyl alcohol) and chemically modified derivatives thereof; poly(acrylic acid) and chemically modified derivatives thereof; poly(hedral oligosilsesquioxane) and chemically modified derivatives thereof; poly(methacrylic acid) and chemically modified derivatives thereof; poly(vinyl-pyrrolidone) and chemically modified derivatives thereof; poly(isopropylacrylamide) and chemically modified derivatives thereof; polyphosphazene and chemically modified derivatives thereof; peptides and chemically modified derivatives thereof; polyaldehyde and chemically modified derivatives thereof; tyrosine-derived polycarbonates and chemically modified derivatives thereof; methacrylate and chemically modified derivatives thereof; polymethacrylate and chemically modified derivatives thereof; N-isopropylacrylamide and chemically modified derivatives thereof;

acrylamide and chemically modified derivatives thereof; polyacrylamide and chemically modified derivatives thereof; acrylate and chemically modified derivatives thereof; polyacrylate and chemically modified derivatives thereof; poly(lactic acid) and chemically modified derivatives thereof; poly(glycolic acid) and chemically modified derivatives thereof; poly(lactide-co-glycolide) and chemically modified derivatives thereof; poly(lactic-co-glycolic acid) and chemically modified derivatives thereof; poly(3, 4-ethylenedioxythiophene) and chemically modified derivatives thereof; graphene oxide and chemically modified derivatives thereof; poly(graphene oxide) and chemically modified derivatives thereof; polycaprolactone and chemically modified derivatives thereof; sodium dodecyl sulfate and chemically modified derivatives thereof; vinyl phosphonic acid and chemically modified derivatives thereof; polydimethylsiloxane and chemically modified derivatives thereof; titanium and chemically modified derivatives thereof; bioactive glass and chemically modified derivatives thereof; carbon nanotubes and chemically modified derivatives thereof; silicone and chemically modified derivatives thereof; silica and chemically modified derivatives thereof; and thiolene materials and chemically modified derivatives thereof.

In another embodiment, the hydrogel materials are formed from mixtures of two or more of the natural hydrogel materials. In another embodiment, the hydrogel materials are formed from mixtures of two or more of the synthetic hydrogel materials. For example, poloxamers include three distinct synthetic materials arranged as triblock copolymers. It is also contemplated that various polymeric materials described herein may be modulated with functional groups to facilitate fabrication of hydrogel materials which exhibit characteristics selected to enhance delivery of the ISV agents, Tregs, antibodies, and cells or to enhance the biocompatibility of the hydrogel material with the biological system within which the hydrogel material is utilized.

Figures 5A, 5B, 5C, 5D:
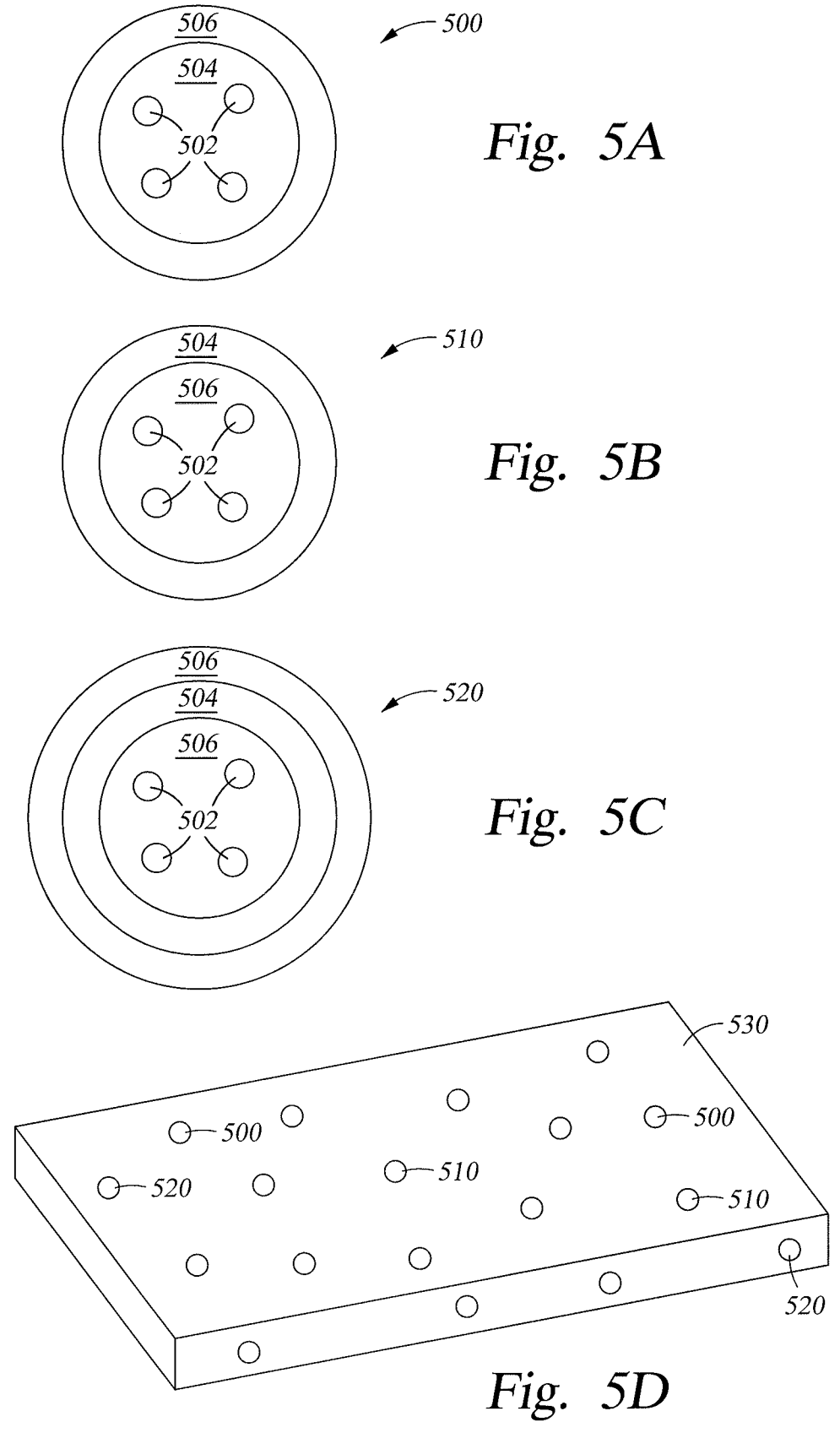
FIG. 5A illustrates a therapeutic delivery vehicle including nanoparticles, a first material layer, and a second material layer, according to embodiments described herein.
FIG. 5B illustrates a therapeutic delivery vehicle including nanoparticles, a first material layer, and a second material layer, according to embodiments described herein.
FIG. 5C illustrates a therapeutic delivery vehicle including nanoparticles, a first material layer, and a second material layer, according to embodiments described herein.
FIG. 5D illustrates a hydrogel system including a bulk hydrogel material and the therapeutic delivery vehicles of FIGS. 5A-5C, according to embodiments described herein.

FIG. 5A illustrates a delivery vehicle 500 for ISV agent, Tregs, antibody, and/or MSC release. The delivery vehicle 500 is fabricated in a manner to enable time delayed and/or continuous release of the ISV agents and/or Tregs antibodies/MSCs. The delivery vehicle 500 includes a plurality of nanoparticles 502, a first material layer 504, and a second material layer 506. The nanoparticles 502 are interdispersed within the first material layer 504 and the first material layer 504 is encapsulated within the second material layer 506.

In one embodiment, ISV agents, such as CsA, tacrolimus, and/or prednisolone, are dispersed within and supported by the nanoparticles 502. In another embodiment, Tregs, antibodies and/or MSCs are dispersed within the nanoparticles 502. In one embodiment, the nanoparticles 502 comprise PLGA, however it is contemplated that other surface eroding materials suitable for utilization in a biological system may be advantageously utilized according to the embodiments described herein.

The first material layer 504 has the nanoparticles 502 disposed therein and in one embodiment, the first material layer 504 comprises an enzymatically degrading PEG material. The second material layer 506 encapsulates the first material layer 504. Either of the first material layer 504 and/or the second material layer 506 are fabricated from one or both of the naturally derived and synthetic hydrogel materials described herein. In one embodiment, the second material layer 506 comprises a hydrolytically degrading PEG material. The enzymatically degrading PEG material and the hydrolytically degrading PEG material have different degradation rates in one embodiment. For example, the hydrolytically degrading PEG material may have a degradation rate greater than a degradation rate of the enzymatically degrading PEG material. In other words, the hydrolytically degrading PEG material decomposes faster than the enzymatically degrading PEG material. In another example, the hydrolytically degrading PEG material may have a degradation rate less than a degradation rate of the enzymatically degrading PEG material. In other words, the hydrolytically degrading PEG material decomposes slower than the enzymatically degrading PEG material. In another embodiment, the enzymatically degrading PEG material and the hydrolytically degrading PEG material have similar degradation rates.

FIG. 5B illustrates a delivery vehicle 510 for ISV agent, Tregs, antibody, and/or MSC release. Similar to the delivery vehicle 500, the delivery vehicle 510 is fabricated in a manner to enable time delayed and/or continuous release of the ISV agents and/or Tregs antibodies/MSCs. The delivery vehicle 510 includes the plurality of nanoparticles 502, the first material layer 504, and the second material layer 506. The nanoparticles 502 are interdispersed within the second material layer 506 and the second material layer 506 is encapsulated within the first material layer 504.

FIG. 5C illustrates a delivery vehicle 520 for ISV agent, Tregs, antibody, and/or MSC release. Similar to the delivery vehicles 500, 510, the delivery vehicle 520 is fabricated in a manner to enable time delayed and/or continuous release of the ISV agents and/or Tregs antibodies/MSCs. The delivery vehicle 520 includes the plurality of nanoparticles 502, the first material layer 504, and a plurality of second material layers 506. The nanoparticles 502 are interdispersed within the second material layer 506 and the second material layer 506 is encapsulated within the first material layer 504. An additional second material layer 506 encapsulates the first material layer 504. In another embodiment, the nanoparticles 502 may be interdispersed within the first material layer 504 and the first material layer 504 may be encapsulated with the second material layer 506. An additional first material layer 504 may encapsulate the second material layer 506.

FIG. 5D illustrates a bulk hydrogel material 530 having a plurality of delivery vehicles disposed therein. In one embodiment, the hydrogel material 530 is a PEG material. In another embodiment, the hydrogel material 530 is a PLGA material. Various different types of delivery vehicles, such as the delivery vehicles 500, 510, and 520 may be dispersed throughout the hydrogel material 530 to application to a PN allograft. In one embodiment, the hydrogel material 530 is photopolymerizable. In operation, after performing a PN allograft, the hydrogel material having drug loaded delivery vehicles disposed therein is injected locally to the nerve cavity around the PN allograft. The hydrogel material is then photopolymerized to improve the structural integrity of the material within the nerve cavity around the PN allograft.

As described above, small molecules can be retained in and released from hydrogel architectures that are more suited to viably maintain encapsulated materials. By utilizing various combinations of enzymatically and hydrolytically degrading PEG materials, in combination with the PLGA material of the nanoparticles, various ISV agents, Tregs, antibodies, and/or MSCs may be released in a time controllable manner via an in situ polymerizable hydrogel material.

PEG hydrogels provide for synthetically modifying the backbone and crosslink architecture, and therefore, the mechanical and diffusive properties of the hydrogel network. The mechanism and kinetics of degradation affect network properties over time as crosslinks break in response to environmental stimuli. Examples of degradation motifs include hydrolysis, thermoresponsive de-gelation, optical cleavage of crosslinks, and enzymatic degradation. Combining the degradation motifs and blending functional PEG copolymers generate hydrogels with complex porosity and mesh size distributions over time and space. Accordingly, any pharmacological compounds loaded within the hydrogel network will be released when crosslink degradation sufficiently opens the network for diffusion.

Enzymatically degradable particles degrade in response to MMPs secreted by the allograft or native axon. Accordingly, successively longer lag times before PLGA particles are exposed and begin to degrade can be achieved. Modulating the particle size distribution provides smooth and tunable release profiles. Release profiles of ISV agents, Tregs, antibodies, MSCs, and cells are a function of particle structure, size, and encapsulating phase composition. For example, the encapsulation of ISV agents loaded PLGA nanoparticles within enzymatically degradable PEG hydrogel particles can be protected by encapsulating the PLGA nanoparticles within a hydrolytically degradable PEG-PLA hydrogel. The PEG-PLA matrix is believed prevent the diffusion of MMPs to the core, thus preventing erosion of the enzymatically degradable encapsulant until the programmed degradation of the PEG-PLA shell is complete.

The injectable delivery system further includes microfluidically-generated microscale particles suspended within a continuous PEG-based hydrogel-forming solution that will be polymerized in situ at the PN allograft site. Immunosuppressive agents or cells may be enclosed within either compartment. Both microscale hydrogel droplets and continuous carrier phase materials are to be crosslinked with a variety of hydrolytically and enzymatically degradable motifs to provide control over the spatial distribution of degradation rate of ISV agents, Tregs, antibodies, MSCs, and other cells.

In-situ delivery of ISV agents, Tregs, antibodies, MSCs, and other cells via the hydrogel materials described herein at the time of allotransplantation are contemplated to reduce or eliminate the probability of graft rejection by the host biological system. It is also contemplated that localized supplemental injections of the ISV agents, Tregs, antibodies, MSCs, and other cells may be utilized at or near the allograft site to further suppress the potential for graft rejection post-transplantation.

In summation, methods and material for localized immunosuppression of PN allografts are described herein. Various immunosuppressive agents may be utilized alone or in combination with one another to facilitate immunosuppression locally to a PN allograft. Materials which provide for delivery of the immunosuppressive agents enable time released and locally controllable delivery which can be utilized to facilitate reinnervation post PN allograft without the risks commonly associated with systemic immunosuppression.

While the foregoing is directed to embodiments of the present disclosure, other and further embodiments of the disclosure may be devised without departing from the basic scope thereof, and the scope thereof is determined by the claims that follow.

What is claimed is:

1. A pharmaceutically acceptable carrier material, comprising:

a first hydrogel material, the first hydrogel material comprising a bulk-eroding hydrogel material comprising one or more of extracellular matrix, collagen, alginate, agarose, peptide-based hydrogels, hyaluronic acid, hyaluronan, keratin, fibronectin, dermatan, poly(sialic acid), fibrin, chitosan, chitin, cholic acid, dextran, dextrin, cellulose, gelatin, gelatinous protein mixtures, laminin, perlecan, aggrecan, glycosaminoglycans, heparin, cholesterol, chondroitin sulfate, polycholesterol, hydroxyapatite, silk, bisphosphonates, tricalcium phosphate, sacran, decellularized extracellular matrix, xanthan gum, starch, pectin, amylopectin, amylose, elastin, and combinations and mixtures thereof, and a plurality of discrete, spherical delivery vehicles doped into the first hydrogel material, the spherical delivery vehicles comprising:

a first layer comprising a second hydrogel material, wherein the second hydrogel material is enzymatically degrading;

a second layer encapsulating the first layer and comprising a third hydrogel material, wherein the third hydrogel material is hydrolytically degrading and different from the first and second hydrogel materials;

a plurality of spherical polymeric nanoparticles disposed in the first layer, the polymeric nanoparticles comprising a fourth hydrogel material; and one or more of immunosuppressive agents, Tregs, antibodies, and mesenchymal stromal cells disposed in each of the plurality of polymeric nanoparticles.

2. The material of claim 1, wherein the fourth hydrogel material comprises a surface-eroding hydrogel material.

3. The material of claim 1, wherein the first hydrogel material is photopolymerizable.

4. The material of claim 1, wherein the first hydrogel material is hydrophilic.

5. The material of claim 1, wherein the first hydrogel material comprises a three-dimensional polymeric network.

6. The material of claim 5, wherein the three-dimensional polymeric network comprises polymer chains cross-linked by covalent bonds.

7. The material of claim 1, wherein the second hydrogel material comprises extracellular matrix.

8. The material of claim 1, wherein the third hydrogel material comprises extracellular matrix.

9. The material of claim 1, wherein the polymeric nanoparticles comprise collagen.

10. The material of claim 1, wherein the first hydrogel material and the second hydrogel material comprise extracellular matrix.

11. The material of claim 1, wherein the polymeric nanoparticles comprise alginate.

12. A pharmaceutically acceptable carrier material, comprising:

a first hydrogel material, the first hydrogel material comprising a bulk-eroding hydrogel material comprising one or more of extracellular matrix, collagen, alginate, agarose, peptide-based hydrogels, hyaluronic acid, hyaluronan, keratin, fibronectin, dermatan, poly(sialic acid), fibrin, chitosan, chitin, cholic acid, dextran, dextrin, cellulose, gelatin, gelatinous protein mixtures, laminin, perlecan, aggrecan, glycosaminoglycans, heparin, cholesterol, chondroitin sulfate, polycholesterol, hydroxyapatite, silk, bisphosphonates, tricalcium phosphate, sacran, decellularized extracellular matrix, xanthan gum, starch, pectin, amylopectin, amylose, elastin, and combinations and mixtures thereof; and a plurality of discrete, spherical delivery vehicles doped into the first hydrogel material, the spherical delivery vehicles comprising:

a first layer comprising a second hydrogel material, wherein the second hydrogel material is enzymatically degrading;

a second layer encapsulating the first layer and comprising a third, hydrogel material, wherein the third hydrogel material is hydrolytically degrading and different from the second hydrogel material;

a plurality of spherical polymeric nanoparticles disposed in the first layer, the polymeric nanoparticles comprising a fourth hydrogel material; and one or more T cells disposed in each of the polymeric nanoparticles.

\* \* \* \* \*